US009782142B2

United States Patent
Nakanishi et al.

(10) Patent No.: US 9,782,142 B2
(45) Date of Patent: Oct. 10, 2017

(54) X-RAY CT SYSTEM

(71) Applicant: Toshiba Medical Systems Corporation, Otawara-shi (JP)

(72) Inventors: Satoru Nakanishi, Utsunomiya (JP); Naruomi Akino, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/749,979

(22) Filed: Jan. 25, 2013

(65) Prior Publication Data

US 2013/0195240 A1 Aug. 1, 2013

(30) Foreign Application Priority Data

Jan. 27, 2012 (JP) ................................. 2012-015128

(51) Int. Cl.
*A61B 6/03* (2006.01)
*A61B 6/00* (2006.01)
(Continued)

(52) U.S. Cl.
CPC ............ *A61B 6/5288* (2013.01); *A61B 6/027* (2013.01); *A61B 6/032* (2013.01); *A61B 6/035* (2013.01);
(Continued)

(58) Field of Classification Search
CPC ........... A61B 6/03; A61B 6/025; A61B 6/032; A61B 6/035; A61B 6/04; A61B 6/0407;
(Continued)

(56) References Cited

U.S. PATENT DOCUMENTS

| 6,418,184 B1 * | 7/2002 | Wang et al. ................. 378/15 |
| 2006/0116567 A1 * | 6/2006 | Nilsen et al. .............. 600/407 |

(Continued)

FOREIGN PATENT DOCUMENTS

| JP | 2003-135443 A | 5/2003 |
| JP | 2009-28065 | 2/2009 |

(Continued)

OTHER PUBLICATIONS

Combined Chinese Office Action and Search Report issued Jul. 2, 2014 in Patent Application No. 201310028481.2 (with English Translation of Category of Cited Documents).

(Continued)

*Primary Examiner* — Glen Kao
(74) *Attorney, Agent, or Firm* — Oblon, McClelland, Maier & Neustadt, L.L.P.

(57) ABSTRACT

In the X-ray CT system according to an embodiment, a control means displaces and images imaging regions in the subject by controlling a top board driver and an imaging means such that the X-rays are projected onto the subject every time a top board is moved by a predetermined transfer amount. An acquiring means acquires projection data of the respective imaging regions. A reconstruction means, based on the projection data, reconstructs tomographic images for each predetermined size of a reconstruction region. In the scan control mode, the control means outputs the transfer amount corresponding to this mode to the top board driver. In the reconstruction control mode, the control means outputs the size of the reconstruction region corresponding to this mode to the reconstruction means.

8 Claims, 14 Drawing Sheets

(51) Int. Cl.
  *A61B 6/04* (2006.01)
  *A61B 6/02* (2006.01)
(52) U.S. Cl.
  CPC .......... *A61B 6/0407* (2013.01); *A61B 6/0457* (2013.01); *A61B 6/503* (2013.01); *A61B 6/5205* (2013.01); *A61B 6/541* (2013.01)
(58) Field of Classification Search
  CPC ... A61B 6/0457; A61B 6/0492; A61B 6/4447; A61B 6/5288; G01N 23/04
  USPC ...... 378/4, 8, 17, 19, 20, 21, 25, 37, 62, 95, 378/98, 98.8, 162, 163, 164, 205, 208, 378/209
  See application file for complete search history.

(56) References Cited

U.S. PATENT DOCUMENTS

| | | | | |
|---|---|---|---|---|
| 2008/0159610 | A1* | 7/2008 | Haas et al. | 382/131 |
| 2009/0000614 | A1* | 1/2009 | Carrano | 128/118.1 |
| 2009/0028289 | A1* | 1/2009 | Tsuyuki et al. | 378/8 |
| 2009/0060125 | A1 | 3/2009 | Tsuyuki et al. | |
| 2010/0074498 | A1* | 3/2010 | Breeding | G06T 11/005 382/131 |
| 2011/0286573 | A1* | 11/2011 | Schretter et al. | 378/4 |

FOREIGN PATENT DOCUMENTS

| | | |
|---|---|---|
| JP | 2009-125250 A | 6/2009 |
| JP | 2010-240387 A | 10/2010 |

OTHER PUBLICATIONS

Office Action issued Nov. 17, 2015 in Japanese Patent Application No. 2012-015128.
Office Action issued Jun. 28, 2016 in Japanese Patent Application No. 2012-015128.

* cited by examiner

FIG. 3

|  | WEIGHT W1 |
|---|---|
| ECG/RESPIRATION GATED EXAMINATION | 1 |
| NON-ECG/NON-RESPIRATION GATED EXAMINATION | 0 |

FIG. 5

| HEART RATE | TRANSFER AMOUNT |
|---|---|
| HR1 | $2\beta 1$ |
| HR2 | $2\beta 2$ |
| ... | ... |
| HRk | $2\beta k$ |
| ... | ... |
| HRn | $2\beta n$ |

FIG. 6

| RESPIRATORY RATE | TRANSFER AMOUNT |
|---|---|
| BR1 | 3$\beta$1 |
| BR2 | 3$\beta$2 |
| ... | ... |
| BRk | 3$\beta$k |
| ... | ... |
| BRn | 3$\beta$n |

FIG. 7

|  | WEIGHT W2 |
|---|---|
| ECG GATED EXAMINATION | 1 |
| NON-ECG GATED EXAMINATION | 0 |

FIG. 8

|  | WEIGHT W3 |
|---|---|
| RESPIRATION GATED EXAMINATION | 0.9 |
| NON-RESPIRATION GATED EXAMINATION | 0.1 |

FIG. 9

| SIZE OF IMAGING REGION | TRANSFER AMOUNT |
|---|---|
| L1 | $4\beta 1$ |
| L2 | $4\beta 2$ |
| ... | ... |
| Lk | $4\beta k$ |
| ... | ... |
| Ln | $4\beta n$ |

FIG. 10

|  | WEIGHT |
|---|---|
| ALL PHASE IMAGING | W4 |
| PARTIAL PHASE IMAGING | W5 |

FIG. 11

| NUMBER OF ROWS | TRANSFER AMOUNT |
|---|---|
| N1 | $5\beta 1$ |
| N2 | $5\beta 2$ |
| ... | ... |
| Nk | $5\beta k$ |
| ... | ... |
| Nn | $5\beta n$ |

X-RAY CT SYSTEM

CROSS-REFERENCE TO RELATED APPLICATION

This application is based upon and claims the benefit of priority from Japanese Patent Application No. 2012-015128, filed Jan. 27, 2012; the entire contents of which are incorporated herein by reference.

FIELD

Embodiments of the present invention relate to an X-ray CT system.

BACKGROUND

As a conventional X-ray CT (computed tomography) system, there is an X-ray CT system that detects X-rays radiated from an X-ray tube onto a subject and transmitted through the subject by means of an X-ray detector, acquires projection data, and reconstructs an image from the acquired projection data.

FIG. 14 illustrates imaging regions. As illustrated in FIG. 14, the radiated X-rays have a cone angle θ such that they spread from the X-ray tube in the body-axis direction of the subject (cone-beam). The imaging regions (Field OF View: FOV) in the subject are provided within the cone angle θ.

A step and shoot type of scan is used in which the imaging regions in the subject are displaced and imaged by radiating the cone-beam onto the subject every time a top is moved in the body-axis direction by a predetermined transfer amount. In addition, such a scan is sometimes referred to as a wide-volume scan.

In the event of considering such a scan, reducing the region overlapped between the adjacent imaging regions and composed upon reconstruction as much as possible contributes to the reduction of radiation exposure. FIG. 14 illustrates the adjacent imaging regions as a region surrounded by bold solid lines and a region surrounded by bold broken lines. Moreover, when the shape of the adjacent imaging regions are both hexagons, the range of the overlap region when imaging is represented as β.

However, different from a helical scan, the more the overlap region is reduced, the worse the continuity between the imaging regions becomes, resulting in the sharp appearance of discontinuity in the imaging region boundary. In order to avoid this, discontinuity in the boundary is obscured by providing an overlap region and carrying out scanning, then smoothly shifting the overlap region (feathering).

However, conventional sagittal/coronal images become hexagons (refer to FIG. 14). Consequently, more projection data for the overlap region must be provided than necessary such that feathering is easily carried out by sufficiently using the projection data of the overlap region. On the other hand, recently, it has become possible to image regions that could not be reconstructed, making it possible to reconstruct a wider range from the projection data of one imaging region. Accordingly, in principle, it has become possible to minimize the overlap region.

However, according to an example of a conventional X-ray CT system for scanning a heart, when dividing the heart into two imaging regions, because the heart is always beating, there are many cases in which the shape of the heart is different in a first imaging region and a second imaging region. In such a case, if the overlap region is minimized, discontinuity in the imaging region boundary sharply appears to deteriorate the image quality.

In another example, the top board has a problem in terms of rigidity. Because the bend amount of the top board cannot be reduced to zero, the larger the range of one imaging region and the longer the distance between the imaging regions, the larger the difference in the bend amounts of the top board becomes; moreover, if the overlap region is minimized, discontinuity in the imaging region boundary sharply appears to deteriorate the image quality.

In addition, according to X-ray detectors of recent years, the X-ray detecting elements are arranged in multiple rows in the body-axis direction. Consequently, the distance between the imaging regions tends to be long, resulting in a problem of discontinuity in the imaging region boundary.

BRIEF DESCRIPTION OF THE DRAWINGS

FIG. 3 illustrates the weights of an ECG (electrocardiogram) gated examination and a respiration gated examination.

FIG. 5 is a table illustrating the correspondence relation between the heart rate and the transfer amount of the top board.

FIG. 6 is a table illustrating the correspondence relation between the respiratory rate and the transfer amount of the top board.

FIG. 7 illustrates the weights of an ECG gated examination according to the second embodiment.

FIG. 8 illustrates the weights of a respiration gated examination.

FIG. 9 is a table illustrating the correspondence relation between the imaging region and the transfer amount of the top board according to the third embodiment.

FIG. 10 illustrates the weights of all phase imaging and partial phase imaging according to the fourth embodiment.

FIG. 11 illustrates the relation table of the number of rows and the transfer amount of the top board according to the fifth embodiment.

DETAILED DESCRIPTION

In the X-ray CT system according to an embodiment, a control means displaces and images imaging regions in the subject by controlling a top board driver and an imaging means such that the X-rays are projected onto the subject every time a top board is moved by a predetermined transfer amount. An acquiring means acquires projection data of the respective imaging regions. A reconstruction means, based on the projection data, reconstructs tomographic images for each predetermined size of a reconstruction region. In the scan control mode, the control means outputs the transfer amount corresponding to this mode to the top board driver. In the reconstruction control mode, the control means outputs the size of the reconstruction region corresponding to this mode to the reconstruction means.

(Configuration)

Hereinafter, various embodiments of the X-ray CT system will be described with reference to the drawings.

First Embodiment

Figure 1:
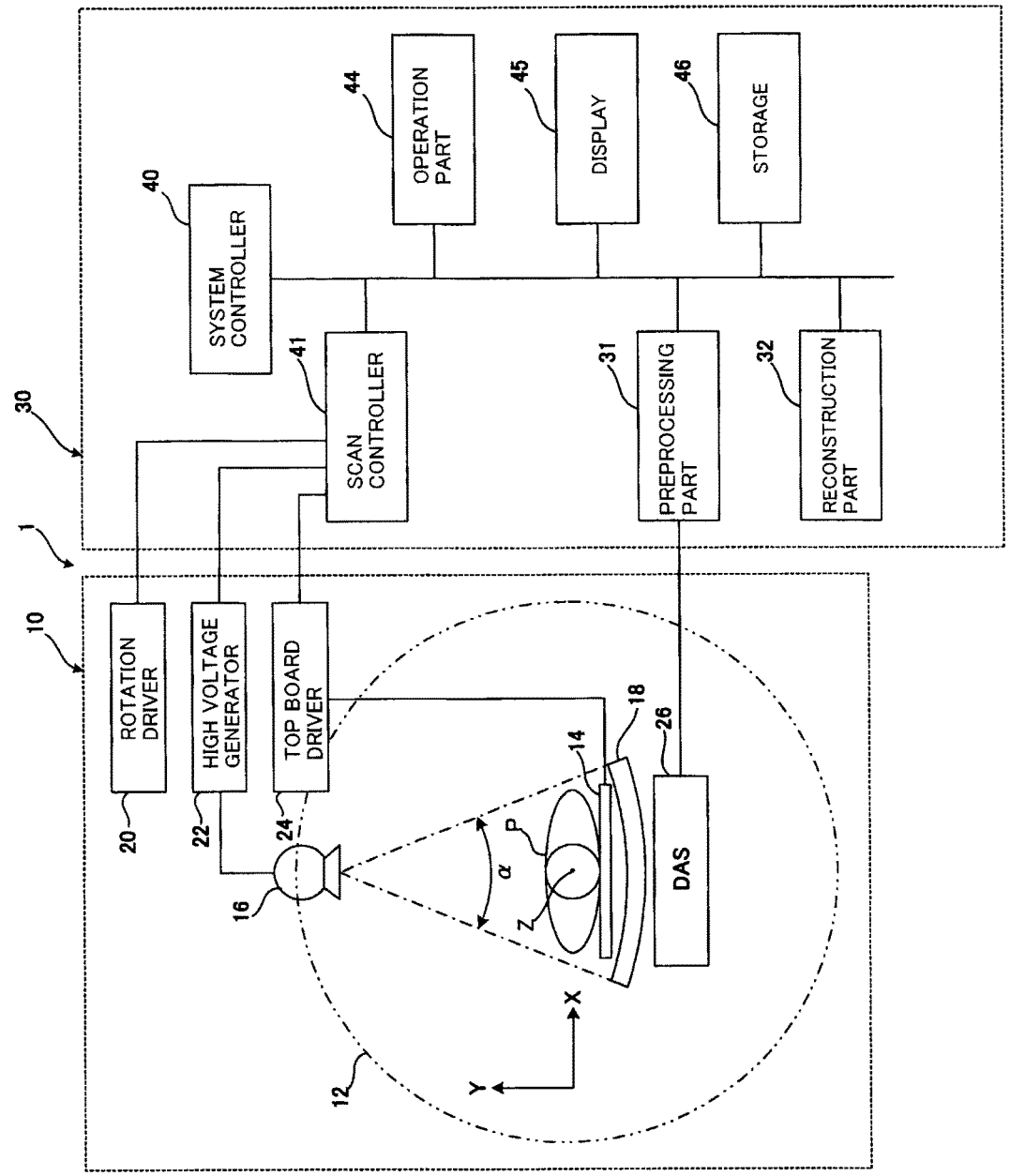
FIG. 1 is a block diagram illustrating the configuration of an X-ray CT system according to the first embodiment.

The configuration of the X-ray CT system according to the first embodiment will be described with reference to FIG. 1. FIG. 1 is a block diagram illustrating the configuration of an X-ray CT system.

As illustrated in FIG. 1, an X-ray CT system 1 comprises a gantry 10 and a console 30.

The gantry 10 comprises a rotation frame 12, an X-ray tube 16, a main detector 18, a trigger detector 19, a rotation driver 20, a high voltage generator 22, and a data acquisition system (DAS) 26.

The main body of the gantry 10 supports an annular or disk-shaped rotation frame 12 such that it is rotatable. A scan region, into which a subject P mounted on the top board 14 is inserted, is formed on the inner peripheral side of the rotation frame 12.

A top board driver 24 is installed in a bed (not illustrated) so as to longitudinally (body-axis direction of the subject P) move the top board 14. In addition, an ascend/descend means (not illustrated) is installed in the bed to vertically (upper and lower directions) slide the top board 14.

Here, an XYZ orthogonal coordinate system is defined. The Z axis is defined as the rotational axis of the rotation frame 12. The top board 14 is arranged such that the longitudinal direction thereof is directed parallel to the Z axial direction. Accordingly, the body axis of the subject P is directed parallel to the Z axis. The X axis is defined as the horizontal axis while the Y axis is defined as the vertical axis.

Further, the X-ray CT system 1 has various types such as a ROTATE/ROTATE type in which the X-ray tube 16 and the main detector 18, etc. are integrated to rotate around the subject and a STATIONARY/ROTATE type in which many detecting elements are arranged in a ring shape and only the X-ray tube 16 rotates around the subject; however, the present embodiment can be applied to any type. Here, the X-ray CT system 1 will be described as the ROTATE/ROTATE type.

The X-ray tube 16 and the main detector 18 are arranged on the rotation frame 12.

Upon receiving a supply of driving signals from the rotation driver 20, the rotation frame 12 continuously rotates the X-ray tube 16 and the main detector 18.

The X-ray tube 16 generates X-rays upon receiving an application of a high voltage and a supply of a filament current from the high voltage generator 22.

The X-ray tube 16 and the main detector 18 are arranged such that they oppose the subject P mounted on the top board 14.

As illustrated in FIG. 1, the main detector 18 is configured by arranging X-ray detecting element groups (a plurality of X-ray detecting elements arranged in the orthogonal direction to the body axis (Z axis) of the subject P) in multiple rows along the Z axis direction. For example, the X-ray detecting elements are arranged in 320 rows at a pitch of 0.5 mm.

In the step and shoot type of X-ray CT system that transfers and images the imaging regions in the subject, every time the top board 14 is moved in the body-axis direction by a predetermined transfer amount, the X-rays (cone-beams) are projected onto the subject P. When scanning is carried out with 0.5 mm*320 rows, if the range of the overlap region when imaging is "β", the transfer amount "X" of the top board 14 is represented by the formula "X=160−β". From this formula, at β=0, the transfer amount "X" becomes 160 mm. In the following embodiments, an explanation is provided assuming that the transfer amount "X" of the top board 14 is no more than 160 mm.

The top board driver 24, in accordance with control by a scan controller 41 within the console 30, moves the top board 14 by a predetermined transfer amount "X" each time. The transfer amount "X" of the top board 14 corresponds to the scan control mode.

Figure 2:
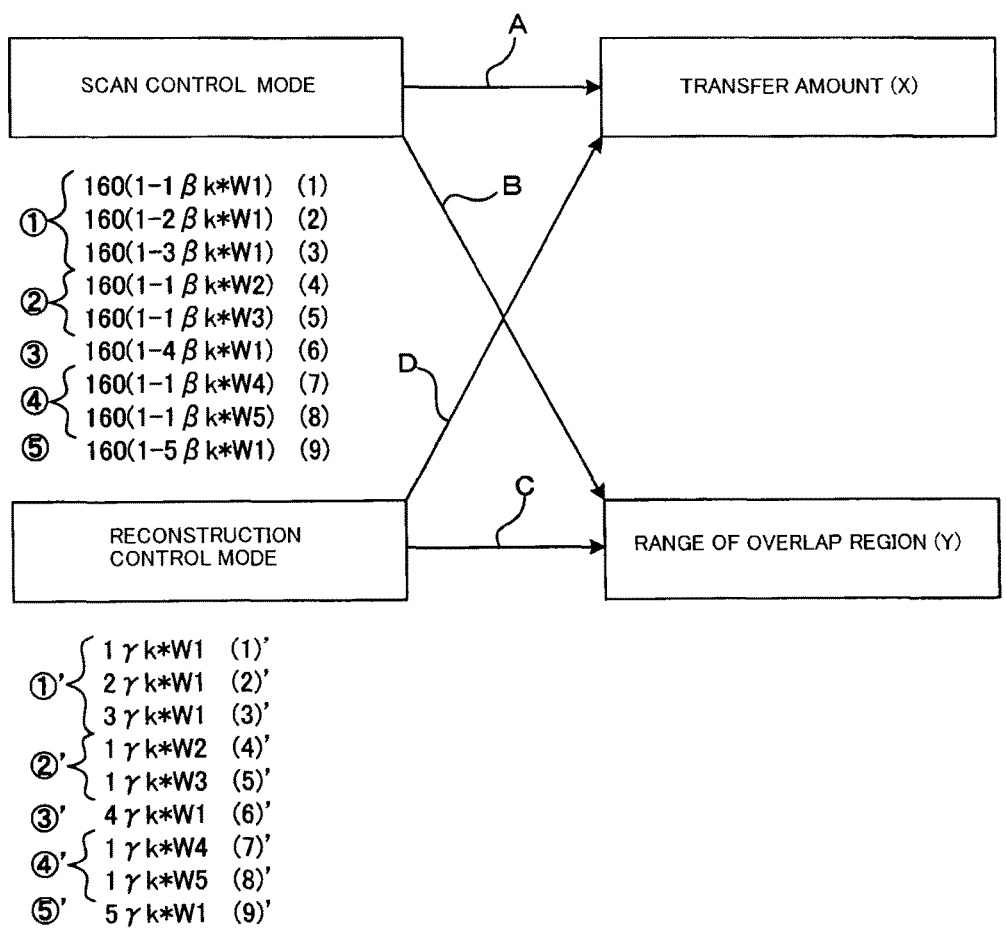
FIG. 2 illustrates the parameters on which the transfer amount of the top board and the range of the overlap region depend.

FIG. 2 illustrates the parameters on which the transfer amount of the top board 14 and the range of the overlap region depend. In FIG. 2, formulas (1) to (9) are illustrated as an example of the scan control mode.

A typical example of the scan control mode is indicated by the formula (1) in which the transfer amount "X" of the top board 14 depends on an ECG gated examination or a respiration gated examination.

In formula (1), the parameter "1βk" is a predetermined value, and selected from (1β1, 1β2, 1βk, 1βn) by operating the operation part 44 by a user (engineer).

FIG. 3 illustrates weights of an ECG gated examination and a respiration gated examination. In FIG. 3, the weight "W1" for the ECG gated examination or the respiration gated examination is illustrated. The weight when the ECG gated examination or the respiration gated examination is specified is "1" (W1=1). In addition, the weight W1 when a non-ECG gated examination or a non-respiration gated examination is specified is "0" (W1=0).

In the scan control mode in which the transfer amount "X" of the top board 14 depends on the predetermined value, the transfer amount "X" of the top board 14 is represented by the formula "X=160−β)"; however, it is represented by the following formula using the above-described parameters "1βk" and "W1".

$$X=160(1-1\beta k*W1) \quad (1)$$

According to the formula (1), when the non-ECG gated examination or the non-respiration gated examination is specified, the transfer amount "X" of the top board 14 becomes "160".

The radiation time interval of the X-rays onto the subject is, for example, ten times per second. According to control by the scan controller 41 within the console 30, the high voltage generator 22 applies a high voltage and supplies a filament current to the X-ray tube 16.

The main detector 18 detects the X-rays generated from the X-ray tube 16 and transmitted through the imaging region, and generates signals in accordance with the intensity of the detected X-rays. A data acquisition system (DAS) 26 is connected to the main detector 18.

According to control by the scan controller 41, the data acquisition system 26 acquires current signals from the main detector 18. The data acquisition system 26 generates projection data made up of digital signals by amplifying the acquired current signals and digitally converting the amplified current signals. Every time projection data is generated, it is supplied to the console 30 via a non-contact data transfer part (not illustrated). Due to repetition of the CT scan, time-series projection data is generated to be supplied to the console 30. The data acquisition system 26 is an example of the acquiring means.

As illustrated in FIG. 1, the console 30 comprises a preprocessing part 31, a reconstruction part 32, a system controller 40, a scan controller 41, an operation part 44, a display 45, and storage 46.

The preprocessing part 31 carries out preprocessing such as logarithmic conversion and sensitivity correction, etc. on projection data supplied from the data acquisition system 26 in real time. Due to the preprocessing, projection data to be used in the image reconstruction is generated.

Based on the projection data with preprocessing applied, the reconstruction part 32 generates CT image data relevant to the subject P in real time. In other words, based on time-series projection data, the reconstruction part 32 reconstructs time-series CT image data (CT values). The reconstruction part 32 is an example of the reconstruction means.

The reconstruction part 32 reconstructs projection data of the respective imaging regions, and composes the overlap region with the adjacent imaging regions overlapping each other. Further, the range of an overlap region when reconstructing to be composed is sometimes referred to as "Y". The magnitude relation between the range "Y" of the overlap region when reconstructing and the range "β" of the overlap region when imaging is represented by the formula "$160 \geq \beta \geq Y$".

The range "Y" of the overlap region when reconstructing corresponds to the reconstruction control mode. FIG. 2 illustrates formulas (1)' to (9)' as an example of the reconstruction control mode. As a representative example of the reconstruction control mode, the range "Y" of the overlap region depends on a predetermined value, and further, it depends on the ECC gated examination or the respiration gated examination. The range "Y" is represented by the following formula.

$$Y = 1\gamma k * W1 \quad (1)'$$

In the formula (1)', the parameter "$1\gamma k$" is a predetermined value and when a user (engineer) inputs data with the operation part 44, this parameter is selected from ($1\gamma 1$, $1\gamma 2$, $1\gamma k$, $1\gamma n$). According to the formula (1)', when the non-ECG gated examination or the non-respiration gated examination is specified, the range "Y" of the overlap region becomes "0".

As the image reconstruction method used by the X-ray CT system, a full scan method and a half scan method are known. The full scan method needs projection data of one circuit around the subject, namely, projection data of about $2\pi$ [rad] in order to reconstruct data of the CT image for one slice. In addition, according to the half scan method, in order to reconstruct the image data of one slice, projection data of $\pi + \alpha$ [rad] ($\alpha$: fan angle) is needed. The present embodiment can be applied to either the full scan method or the half scan method.

The system controller 40 functions as the center of the X-ray CT system 1. Specifically, the system controller 40 reads the control program stored in the storage 46, loads the control program into memory, and controls the respective parts according to the loaded control program. This allows the system controller 40 to carry out CT scanning.

In addition, upon receiving a scan control mode in which the transfer amount "X" depends on the predetermined value "$1\beta k$", the system controller 40 derives the transfer amount "X" from the above-described formula (1), and outputs the derived transfer amount "X" to the scan controller 41.

In order to carry out CT scanning, the scan controller 41 controls the gantry 10 (the rotation driver 20, the high voltage generator 22, the top board driver 24, and the data acquisition system 26). The scan controller 41 outputs the transfer amount "X" derived by the scan controller 41 to the top board driver 24. The top board driver 24 moves the top board 14 by the transfer amount "X" each time.

Further, the system controller 40 and the scan controller 41 are sometimes referred to as a control means.

The operation part 44 receives various instructions and information input from the operator. For example, the operation part 44 inputs the predetermined value "$1\beta k$" via an input device by the user. As an input device, a keyboard, a mouse, a switch, etc. are available.

The display 45 displays the CT images on a display device. As a display device, for example, a CRT display, an LCD, an organic EL display, a plasma display, etc. are available.

The storage 46 stores the projection data and the CT image data. In addition, the storage 46 stores the control program in advance. Further, the storage 46 may store the weight "W1" and the transfer amount "$1\beta k$" in advance.

Hereinbefore, the scan control mode is indicated in which the transfer amount "X" of the top board 14 depends on the ECG gated examination or the respiration gated examination, and the configuration is described in which the top board 14 is moved by the transfer amount "X" corresponding to respective scan control modes each time; however, not limited to these, it is possible to provide a scan control mode depending on the ECG gated examination and the respiration gated examination, and to move the top board 14 by the transfer amount "X" corresponding to this scan control mode each time.

[Operation]

Figure 4:
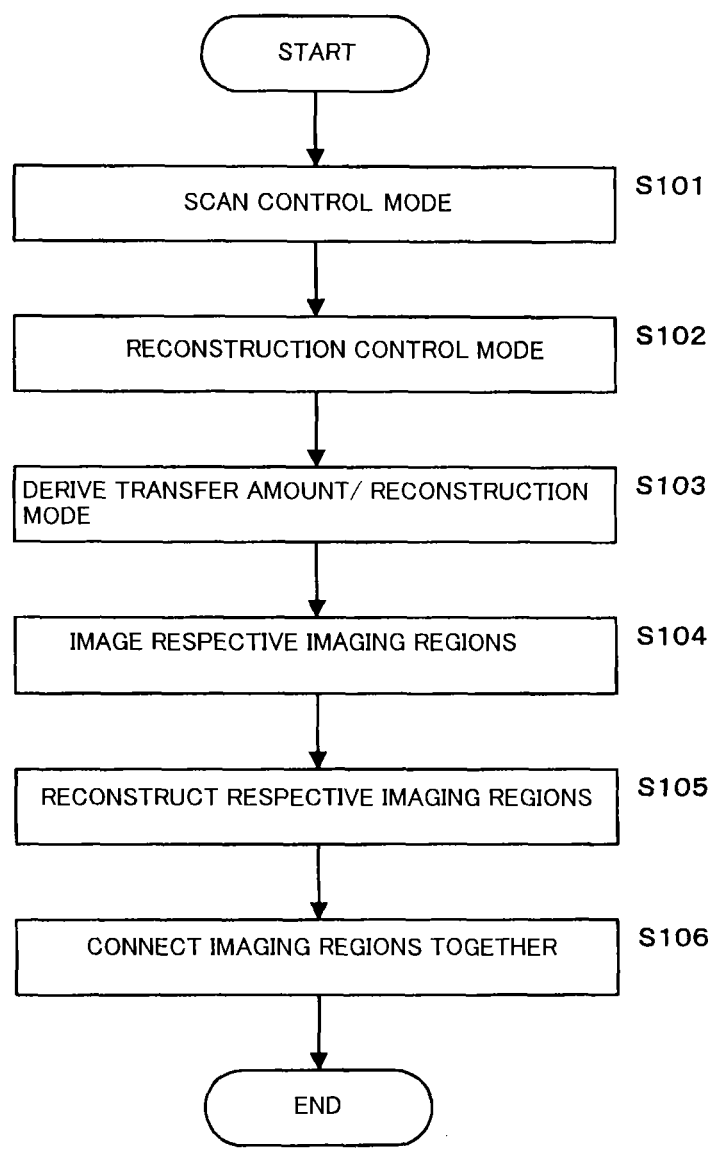
FIG. 4 is a flow chart illustrating the operation of an X-ray CT system.

Next, the CT scan to be carried out by the X-ray CT system 1 will be described with reference to FIG. 4. FIG. 4 is a flow chart illustrating the operation of the X-ray CT system 1. Here, as a representative example of the scan control mode, a mode will be described in which the transfer amount "X" of the top board 14 depends on the ECG gated examination or the respiration gated examination and further depends on the predetermined value "$1\beta k$."

(S101)

Due to the operation of the operation part 44, the scan control mode is specified to the system controller 40. In addition, due to the operation of the operation part 44, the predetermined value "$1\beta k$" is input.

(S102)

About this time, due to the operation of the operation part 44, the reconstruction control mode is specified to the system controller 40. Due to the operation of the operation part 44, "$1\gamma k$" is input.

(S103)

When the non-ECG gated examination or the non-respiration gated examination is specified, the system controller 40 derives the adjusted transfer amount "X" of the top board 14 according to the formula (1) based on the parameters "W1" and "$1\beta k$". Further, when the non-ECG gated examination or the non-respiration gated examination is specified, the system controller 40 derives the adjusted range "Y" of the overlap region according to the formula (1)' based on the parameters "W1" and "$1\gamma k$".

(S104)

The system controller 40 outputs the derived transfer amount "X" to the scan controller 41. The scan controller 41 displaces and images the imaging regions by projecting the X-rays onto the subject every time the top board driver 24 moves the top board 14 by the transfer amount "X". This allows the data acquisition system 26 to acquire the projection data of respective imaging regions.

(S105)

The system controller 40 instructs the reconstruction part 32 to carry out reconstruction. Based on the projection data of the respective imaging regions, the reconstruction part 32 reconstructs tomographic images of the subject for each size of the imaging regions. In addition, using the range "Y" of the overlap region, the reconstruction part 32 composes (performs feathering) the overlap region.

(S106)

In addition, the reconstruction part 32 connects the tomographic images of the imaging regions together. Because the respective imaging regions are imaged every time the top board 14 is moved by the adjusted transfer amount "X" each time, discontinuity in the boundary parts between the imaging regions is avoided, making it possible to prevent deterioration in the image quality. Further, because the overlap regions are composed (by feathering) using the range "Y" of the adjusted overlap region, this avoids discontinuity in the boundary part between the imaging regions, making it possible to prevent deterioration in the image quality.

Modified Example 1: Example in which the Transfer Amount of the Top Board Depends on the Heart Rate In the above-described embodiment, the scan control mode in which the transfer amount "X" of the top board 14 depends on the predetermined value "1βk" is explained; however, not limited to this, a scan control mode in which the transfer amount "X" depends on the heart rate, that is, the beats per minute (BPM), may be available.

Next, with reference to FIG. 5, a modified example 1 will be described in which the top board 14 is moved by a predetermined transfer amount "X" each time based on the scan control mode in which the transfer amount "X" of the top board 14 depends on the heart rate. FIG. 5 is a table illustrating the correspondence relation between the heart rate and the transfer amount "X" of the top board 14.

In the table illustrated in FIG. 5, the transfer amounts "2β1", "2β2", ..., "2βk", ..., "2βn" correspond to the heart rates "HR1", "HR2", ..., "HRk", ..., "HRn", respectively. Generally, the higher the heart rate, the higher the possibility of arising a difference in the shape between the imaging regions and the larger the degree of the difference becomes; therefore, it is better to make the transfer amount "2βk" smaller.

In the scan control mode in which the transfer amount "X" of the top board 14 depends on the heart rate, using the above-described parameters "2βk" and "W1", the transfer amount "X" of the top board 14 is represented by the following formula (refer to FIG. 2).

$$X=160(1-2\beta k*W1) \quad (2)$$

According to the formula (2), when the non-ECG gated examination or the non-respiration gated examination is specified, the transfer amount "X" of the top board 14 becomes "160".

Upon receiving the scan control mode in which the transfer amount "X" depends on the heart rate "HRk", the system controller 40 derives the transfer amount "2βk" corresponding to the heart rate from the table illustrated in FIG. 5, further derives the transfer amount "X" from the above-described formula (2), and outputs the derived transfer amount "X" to the scan controller 41.

The scan controller 41 outputs the transfer amount "X" derived from the scan controller 41 to the top board driver 24. The top board driver 24 moves the top board 14 by the transfer amount "X" each time.

The reconstruction part 32 reconstructs images according to the reconstruction control mode based on the projection data of the imaging regions, and composes the overlap regions.

An example of the reconstruction control mode in this case is indicated in the following formula (refer to FIG. 2).

$$Y=2\gamma k*W1 \quad (2)'$$

Further, the parameters "2γ1", "2γ2", ..., "2γk", ... "2γn" correspond to the heart rates "HR1", "HR2", ..., "HRk", ..., "HRn", respectively, and are stored in the internal memory of the system controller 40 or the storage 46 as a table.

Upon receiving instructions from the system controller 40, the reconstruction part 32 composes (by feathering) the overlap regions upon reconstruction. Because the range "Y" of the overlap region when reconstructing, discontinuity in the boundary part between the imaging regions is avoided, making it possible to prevent deterioration in the image quality.

Modified Example 2: Example in which the Transfer Amount of the Top Depends on the Respiratory Rate In the above-described Modified Example 1, an example of the scan control mode is described in which the transfer amount "X" of the top board 14 depends on the heart rate; however, a scan control mode may be available in which the transfer amount "X" of the top board 14 depends on the respiratory rate.

Next, based on the scan control mode in which the transfer amount "X" of the top board 14 depends on the respiratory rate, Modified Example 2 in which the top board 14 is moved by a predetermined transfer amount "X" each time will be described with reference to FIG. 6. FIG. 6 is a table illustrating the correspondence relation between the respiratory rate and the transfer amount "X" of the top board.

As illustrated in FIG. 6, the transfer amounts "3β1", "3β2", ..., "3βk", ..., "3βn" correspond to the respiratory rates "RR1", "RR2", ..., "RRk", ..., "RRn", respectively. Generally, the higher the respiratory rate, the higher the possibility of arising a difference in the shape between the imaging regions and the larger the degree of the difference becomes; therefore, it is better to make the transfer amount "3βk" smaller.

In the scan control mode in which the transfer amount "X" of the top board 14 depends on the respiratory rate, using the above-described parameters "3βk" and "W1", the transfer amount "X" of the top board 14 is represented by the following formula.

$$X=160(1-3\beta k*W1) \quad (3)$$

According to the formula (3), when the non-ECG gated examination or the non-respiration gated examination is specified, the transfer amount "X" of the top board 14 becomes "160".

Upon receiving the scan control mode in which the transfer amount "X" depends on the respiratory rate "RRk", the system controller 40 derives the transfer amount "3βk" corresponding to the respiratory rate from the table illustrated in FIG. 6, further derives the transfer amount "X" from the above-described formula (3), and outputs the derived transfer amount "X" to the scan controller 41.

The scan controller 41 outputs the transfer amount "X" derived from the scan controller 41 to the top board driver 24. The top board driver 24 moves the top board 14 by the transfer amount "X" each time.

The reconstruction part 32 reconstructs images according to the reconstruction control mode based on the projection data of the imaging regions and composes the overlap regions.

An example of the reconstruction control mode in this case is indicated in the following formula (refer to FIG. 2).

$$Y=3\gamma k*W1 \quad (3)'$$

Further, the parameters "3γ1", "3γ2", . . . , "3γk", . . . "3γn" correspond to the heart rates "HR1", "HR2", . . . , "HRk", . . . , "HRn", respectively, and are stored in the internal memory of the system controller 40 or the storage 46 as a table.

Upon receiving instructions from the system controller 40, the reconstruction part 32 composes (by feathering) the overlap regions when reconstructing. Because the range "Y" of the overlap region upon reconstruction is adjusted, discontinuity in the boundary part between the imaging regions is avoided, making it possible to prevent deterioration in the image quality.

Second Embodiment: Configuration in which the Weight of the ECG Gated Examination and the Weight of the Respiration Gated Examination are Different In the above-described first embodiment and the modified examples, the weight when the ECG gated examination is specified and the weight when the respiration gated examination is specified are defined as the same "W1"; however, the weight when the ECG gated examination is specified and the weight when the respiration gated examination is specified may be different; in other words, the weight when the ECG gated examination is specified is defined as "W2", and the weight when the respiration gated examination is specified is defined as "W3".

Next, the X-ray CT system according to the second embodiment will be described with reference to FIG. 7 and FIG. 8. Further, in the second embodiment, the configuration different from the first embodiment is mainly described, with the explanation of the same configuration herein omitted.

FIG. 7 illustrates the weight of the ECG gated examination. As illustrated in FIG. 7, the weight W2 of the ECG gated examination is "1", while the weight W2 of non-ECG gated examination is "0".

In the scan control mode in which the transfer amount "X" of the top board 14 depends on the predetermined value, using the parameters "1βk" and "W2", the transfer amount "X" of the top board 14 is represented by the following formula (refer to FIG. 2).

$$X=160(1-1\beta k*W2) \quad (4)$$

FIG. 8 illustrates the weight of the respiration gated examination. As illustrated in FIG. 8, the weight W3 of the ECG gated examination is "0.9", while the weight W3 of the non-ECG gated examination is "0.1".

In the scan control mode in which the transfer amount "X" of the top board 14 depends on the predetermined value, using the parameters "1βk" and "W3", the transfer amount "X" of the top board 14 is represented as an example by the following formula (refer to FIG. 2).

$$X=160(1-1\beta k*W3) \quad (5)$$

Upon receiving the scan control mode in which the transfer amount "X" depends on the predetermined value "1βk", the system controller 40 derives the transfer amount "X" by the above-described formula (4) and/or (5), and outputs the derived transfer amount "X" to the scan controller 41. The scan controller 41 outputs the transfer amount "X" derived from the scan controller 41 to the top board driver 24. The top board driver 24 moves the top board 14 by the transfer amount "X" each time.

The reconstruction part 32 reconstructs images according to the reconstruction control mode based on the projection data of the imaging regions and composes the overlap regions.

An example of the reconstruction control mode in this case is indicated in the following formula (refer to FIG. 2).

$$Y=1\gamma k*W2 \quad (4)'$$

$$Y=1\gamma k*W3 \quad (5)'$$

Upon receiving instructions from the system controller 40, the reconstruction part 32 composes (by feathering) the overlap regions upon reconstruction. Because the range "Y" of the overlap region upon reconstruction is adjusted, discontinuity in the boundary part between the imaging regions is avoided, making it possible to prevent deterioration in the image quality.

Third Embodiment: Configuration in which the Transfer Amount of the Top Board Depends on the Range of the Imaging Regions In the above-described embodiment, in the scan control mode in which the transfer amount "X" of the top board 14 depends on the predetermined value "1βk", the transfer amount "X" of the top board 14 is derived from the formulas (1) to (5); however, in the scan control mode in which the transfer amount "X" of the top board 14 depends on the range of the imaging regions, the transfer amount "X" of the top board 14 may be derived from the formula described later.

Next, the X-ray CT system according to the third embodiment will be described with reference to FIG. 9. Further, in the third embodiment, the configuration different from the first embodiment is mainly described, with the explanation of the same configuration herein omitted.

As illustrated in FIG. 9, the transfer amounts "4β1", "4β2", . . . , "4βk", . . . , "4βn" correspond to the ranges "L1", "L2", . . . , "Lk", . . . , "Ln" of the imaging regions, respectively. Generally, the larger the range of the imaging regions, the higher the possibility of arising a difference in the shape between the imaging regions, and the larger the degree of the difference becomes; therefore, it is better to make the transfer amount "4βk" smaller.

In the scan control mode in which the transfer amount "X" of the top board 14 depends on the range of the imaging regions, using the above-described parameters "4βk" and "W1", the transfer amount "X" of the top board 14 is represented by the following formula (refer to FIG. 2).

$$X=160(1-4\beta k*W1) \quad (6)$$

Upon receiving the scan control mode in which the transfer amount "X" depends on the range "Lk" of the imaging region, the system controller 40 derives the transfer amount "4βk" corresponding to the range of the imaging region from the table illustrated in FIG. 9, further derives the transfer amount "X" from the above-described formula (6), and outputs the derived transfer amount "X" to the scan controller 41.

The scan controller 41 outputs the transfer amount "X" derived from the scan controller 41 to the top board driver 24. The top board driver 24 moves the top board 14 by the transfer amount "X" each time.

The scan control mode in which the transfer amount "X" of the top board 14 depends on the range of the imaging region is indicated; however, the scan control mode may be available in which the transfer amount "X" of the top board 14 depends on any one of the conformation of the subject, the size of the imaging site, and the size of the region of interest (ROI), or a combination of two or more thereof.

The reconstruction part 32 reconstructs images according to the reconstruction control mode based on the projection data of the imaging regions and composes the overlap regions.

An example of the reconstruction control mode in this case is indicated in the following formula (refer to FIG. 2).

$$Y=4\gamma k*W1 \tag{6}'$$

Further, the parameters "4γ1", "4γ2", ..., "4γk", ... "4γn" correspond to the ranges "L1", "L2", ..., "Lk", ..., "Ln" of the imaging regions, respectively, and are stored in the internal memory of the system controller 40 or the storage 46 as a table.

Upon receiving instructions from the system controller 40, the reconstruction part 32 composes (by feathering) the overlap regions upon reconstruction. Because the range "Y" of the overlap region upon reconstruction is adjusted, discontinuity in the boundary part between the imaging regions is avoided, making it possible to prevent deterioration in the image quality.

Fourth Embodiment: Configuration in which the Transfer Amount of the Top Board Depends on all Phase Imaging/Partial Phase Imaging In imaging of a body part such as a heart, a lung, etc. that are periodically moving, all phase imaging for taking images including all of one heart beat phase or one respiration phase, and partial phase imaging for taking images of a specific heart beat phase or a specific respiration phase are used.

In the above-described embodiments, the scan control modes in which the transfer amount "X" of the top board 14 depends on the predetermined value "1βk", etc. are described; however, a scan control mode in which the transfer amount "X" depends on all phase imaging or partial phase imaging may be available.

Next, the X-ray CT system according to the fourth embodiment will be described with reference to FIG. 10. Further, in the fourth embodiment, the configuration different from the first embodiment is mainly described, with the explanation of the same configuration herein omitted.

FIG. 10 illustrates the weights of all phase imaging and partial phase imaging. As illustrated in FIG. 10, the weight of all phase imaging is "W4", while the weight of partial phase imaging is "W5".

In the scan control mode in which the transfer amount "X" of the top board 14 depends on all phase imaging, using the parameters "1βk" and "W4", the transfer amount "X" of the top board 14 is represented by the following formula (refer to FIG. 2).

$$X=160(1-1\beta k*W4) \tag{7}$$

Further, in the scan control mode in which the transfer amount "X" of the top board 14 depends on partial phase imaging, using the parameters "1βk" and "W5", the transfer amount "X" of the top board 14 is represented by the following formula (refer to FIG. 2).

$$X=160(1-1\beta k*W5) \tag{8}$$

Upon receiving the scan control mode in which the transfer amount "X" depends on all phase imaging or partial phase imaging, the system controller 40 derives the transfer amount "X" by the above-described formula (7) or (8), and outputs the derived transfer amount "X" to the scan controller 41. The scan controller 41 outputs the transfer amount "X" derived from the scan controller 41 to the top board driver 24. The top board driver 24 moves the top board 14 by the transfer amount "X" each time.

The reconstruction part 32 reconstructs images according to the reconstruction control mode based on the projection data of the imaging regions and composes the overlap regions.

An example of the reconstruction control mode in this case is indicated in the following formula (refer to FIG. 2).

$$Y=1\gamma k*W4 \tag{7}'$$

$$Y=1\gamma k*W5 \tag{8}'$$

Upon receiving instructions from the system controller 40, the reconstruction part 32 composes (by feathering) the overlap regions upon reconstruction. Because the range "Y" of the overlap region upon reconstruction is adjusted, discontinuity in the boundary part between the imaging regions is avoided, making it possible to prevent deterioration in the image quality.

Fifth Embodiment: Configuration in which the Transfer Amount of the Top Board Depends on the Number of Rows of X-Ray Detecting Element Groups In the event of carrying out scanning with 0.5 mm×320 rows, in order to make the range β of the overlap region upon imaging to be zero (β=0), the transfer amount "X" of the top board 14 becomes 160 mm. In the event of carrying out scanning with 0.5 mm×160 rows, the transfer amount "X" becomes 80 mm. Accordingly, in the event of carrying out scanning with 320 rows rather than the event of carrying out scanning with 160 rows, the bend amount of the top board 14 makes a greater impact on the images. Therefore, it is better to avoid discontinuity in the boundary part between imaging regions by making the transfer amount "X" of the top board 14 smaller. In other words, the transfer amount "X" of the top board 14 may be derived by setting the relation between the number of rows N and the optimum transfer amount "X" in advance.

Next, the X-ray CT system according to the fifth embodiment will be described with reference to FIGS. 11 to 13. Further, in the fifth embodiment, the configuration different from the first embodiment is mainly described, with the explanation of the same configuration herein omitted.

FIG. 11 illustrates the relation table of the number of rows of the X-ray detecting element groups and the transfer amount "X" of the top board. As illustrated in FIG. 11, the transfer amounts of the top board 14 "X" "5β1", "5β2", ..., "5βk", ..., "5βn" correspond to the numbers of rows "N1", "N2", ..., "Nk", ..., "Nn", respectively.

Figure 12:
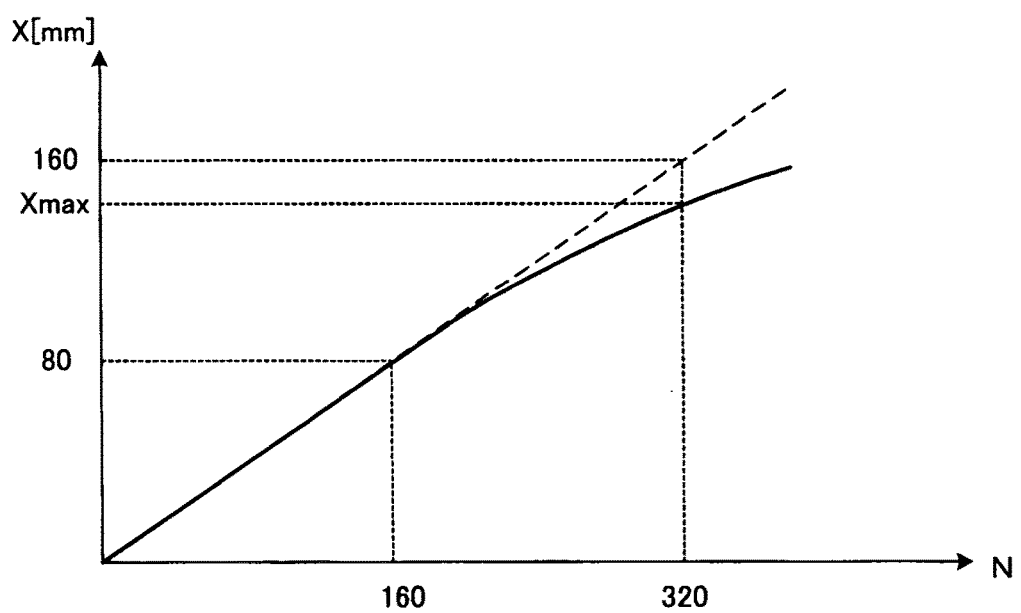
FIG. 12 illustrates the N-X coordinates representing the relation table.
Figure 13:
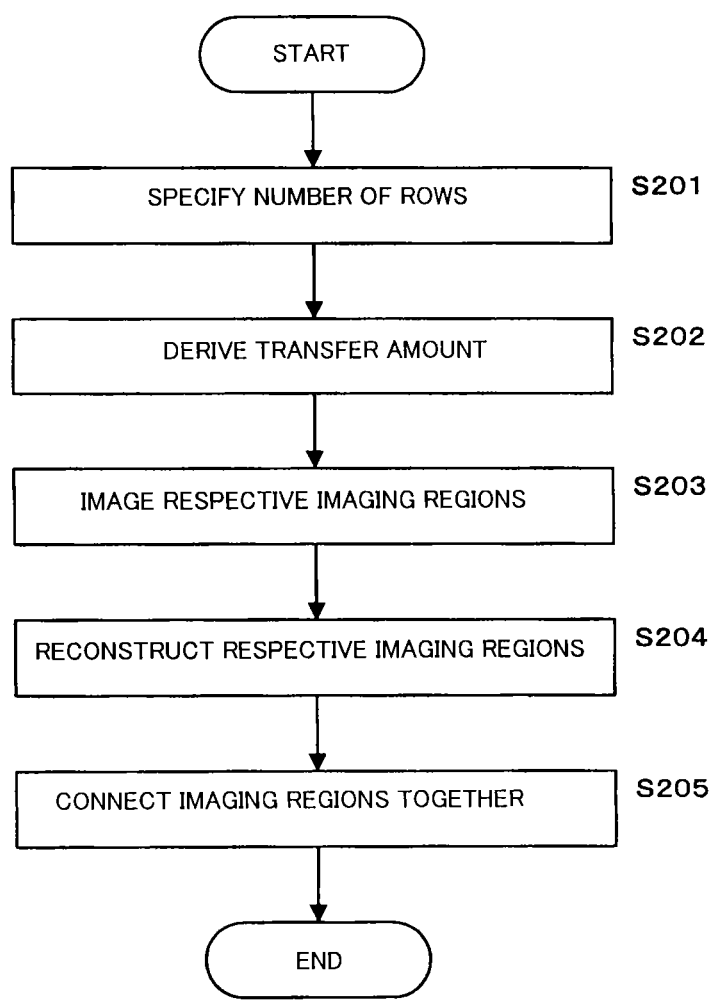
FIG. 13 is a flow chart illustrating the operation of an X-ray CT system.
Figure 14:
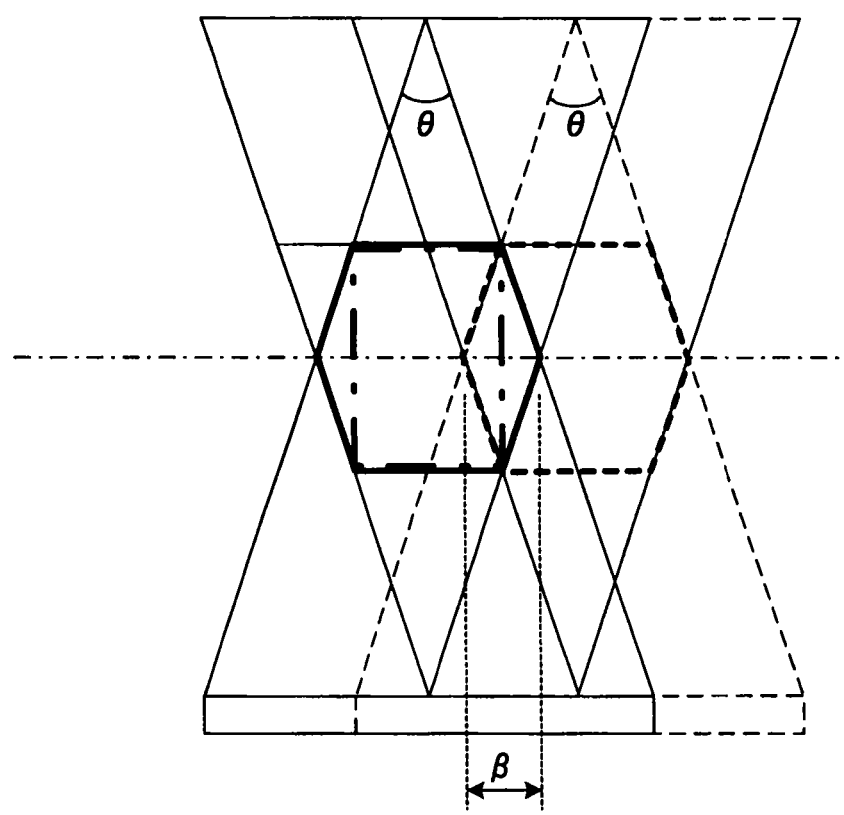
FIG. 14 illustrates the imaging regions.

FIG. 12 illustrates the above-described table represented by N-X coordinates. In FIG. 12, the horizontal axis indicates the number of rows N, while the vertical axis indicates the transfer amount "X", the broken line indicates the transfer amount "X" (non-optimized transfer amount "X") when the range β of the overlap region upon imaging is zero (β=0), and the solid line indicates the transfer amount "X" (optimized transfer amount "X") optimized in accordance with the number of rows.

As illustrated in FIG. 12, up to the 160th rows (N≤160), there is little difference between the optimized transfer amount "X" of the top board 14 and the non-optimized transfer amount "X" thereof; however, after the 160th row (N>160), the optimized transfer amount "X" becomes smaller than the non-optimized transfer amount "X".

In the scan control mode in which the transfer amount "X" of the top board 14 depends on the number of rows of the X-ray detecting element groups, using the parameters "5βk" and "W1", as an example, the transfer amount "X" of the top board 14 is represented by the following formula (refer to FIG. 2).

$$X=160(1-5\beta k*W1) \quad (9)$$

Upon receiving the scan control mode in which the transfer amount "X" depends on the number of X-ray detecting element groups, the system controller 40 derives the transfer amount "X" "5βk" corresponding to the number of the rows from the relation table illustrated in FIG. 11, further derives the transfer amount "X" from the above-described formula (9), then outputs the derived transfer amount "X" to the scan controller 41.

The scan controller 41 outputs the transfer amount "X" derived by the scan controller 41 to the top board driver 24. The top board driver 24 moves the top board 14 by the transfer amount "X" each time.

The reconstruction part 32 reconstructs images according to the reconstruction control mode based on the projection data of the imaging regions and composes the overlap regions.

An example of the reconstruction control mode in this case is indicated in the following formula (refer to FIG. 2).

$$Y=5\gamma k*W1 \quad (9)'$$

Further, the parameters "5γ1", "5γ2", ..., "5γk", ... "5γn" correspond to the numbers of rows "N1", "N2", ..., "Nk", ..., "Nn", respectively, and are stored in the internal memory of the system controller 40 or the storage 46 as a table.

Upon receiving instructions from the system controller 40, the reconstruction part 32 composes (by feathering) the overlap regions upon reconstruction. Because the range "Y" of the overlap region is adjusted upon reconstruction, discontinuity in the boundary part between the imaging regions is avoided, making it possible to prevent deterioration in the image quality.

Next, the CT scan to be carried out by this X-ray CT system 1 will be described with reference to FIG. 13. FIG. 13 is a flow chart illustrating the operation of the X-ray CT system.

(S201)

Due to the operation of the operation part 44, the number of rows N of the X-ray detecting element groups is specified to the system controller 40.

(S202)

When the number of rows N of the X-ray detecting element groups is specified, the system controller 40 derives the adjusted transfer amount "5βk" of the top board 14 corresponding to the rows N of the X-ray detecting element groups according to the relation table illustrated in FIG. 11. Further, the system controller 40 derives the transfer amount "X" of the top board 14 according to formula (9) based on "5βk".

(S203)

The system controller 40 outputs the derived transfer amount "X" to the scan controller 41. The scan controller 41 displaces and images the imaging regions by projecting the X-rays onto the subject every time the top board driver 24 moves the top board 14 by the transfer amount "X" each time. This allows the data acquisition system 26 to acquire the projection data of respective imaging regions.

(S204)

The system controller 40 instructs the reconstruction part 32 to carry out reconstruction. Based on the projection data of respective imaging regions, the reconstruction part 32 reconstructs tomographic images of the subject for each size of imaging regions according to formula (9)'.

(S205)

In addition, the reconstruction part 32 connects the tomographic images of the imaging regions together. Because the respective imaging regions are imaged every time the top board 14 is moved by the adjusted transfer amount "X" each time, discontinuity in the boundary part between the imaging regions is avoided, making it possible to prevent deterioration in the image quality.

In this fifth embodiment, according to the relation table, the adjusted transfer amount "X" of the top board 14 corresponding to the number of the rows N of the X-ray detecting element groups is derived; however, the transfer amount "X" of the top board 14 may be derived by combining the scan control mode explained in the first embodiment to the fourth embodiment with the above-described relation table.

(Aspect of Deriving the Range of the Overlap Region)

In the above-described first to fifth embodiments, a configuration is indicated wherein the system controller 40 derives the transfer amount "X" of the top board 14 using the parameters "W1" to "W5", "1βk" to "5βk", and formulas (1) to (9) (route "A" illustrated in FIG. 2). Not limited to this, from these parameters and formulas, the system controller 40 may derive the range "Y" of the overlap region upon reconstruction (route "B" illustrated in FIG. 2).

In addition, a configuration is indicated wherein the system controller 40 derives the range "Y" of the overlap region upon reconstruction using parameters "W1" to "W5", "1βk" to "5βk", and formulas (1)' to (9)' (route "C" illustrated in FIG. 2). Not limited to this, from these parameters and formulas, the system controller 40 may derive the transfer amount "X" of the top board 14 (route "D" illustrated in FIG. 2).

Further, a configuration is indicated wherein the transfer amount "X" of the top board 14 and the range "Y" of the overlap region upon reconstruction are derived, while making the scan control mode and the reconstruction control mode independent from each other; however, the transfer amount "X" of the top board 14 and the range "Y" of the reconstruction overlap region may be derived, while making the scan control mode and the reconstruction control mode related to each other.

Further, according to the description of the above-described embodiment, a scan control mode is indicated wherein the transfer amount "X" of the top board 14 depends on one of the predetermined value, the heart rate, the respiratory rate, the ECG gated examination, the respiration gated examination, all phase imaging, and partial moving imaging; however, a scan control mode that depends on a combination of two or more thereof may be available, and based on these scan control modes, the transfer amount "X" of the top board 14 may be derived.

Further, in the above-described embodiment, a reconstruction control mode is indicated wherein the range "Y" of the overlap region upon reconstruction depends on one of the predetermined value, the heart rate, the respiratory rate, the ECG gated examination, the respiration gated examination, all phase imaging, partial phase imaging, and the size of the imaging region; however, a reconstruction control mode that depends on a combination of two or more thereof may be available, and based on these reconstruction control modes, the range "Y" of the overlap region upon reconstruction may be derived.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of embodiments described herein may be made without departing from the spirit of the inventions. The accompanying claims and their equivalents are intended to cover such forms or modifications as would fall within the scope and spirit of the inventions.

What is claimed is:

1. An X-ray CT system, comprising:
a top board on which a subject is mounted,
a top board driver configured to move a top in a longitudinal direction of the top board,
an imaging means including an X-ray tube and an X-ray detecting means configured to detect X-rays projected from the X-ray tube and transmitted through the subject,
a control means configured to displace and image imaging regions in the subject by controlling the top board driver and the imaging means such that the X-rays are projected onto the subject every time the top board is moved in the longitudinal direction of the top board by a predetermined transfer amount,
an acquiring means configured to acquire projection data of the respective imaging regions, and
a control means configured to change overlap regions with an adjacent pair of the imaging regions overlapping each other according to a type of scan by which possible occurrence of body movement in the subject is estimated.

2. The X-ray CT system according to claim 1, further comprising a reconstruction means configured to, based on the projection data of the respective imaging regions, reconstruct tomographic images of the subject for each predetermined size of a reconstruction region, wherein
the control means includes a plurality of scan control modes and a plurality of reconstruction control modes, and
when one of the scan control modes is specified, the control means outputs to the top board driver the transfer amount corresponding to the one of the scan control modes, and
when one of the reconstruction control modes is specified, the control means outputs to the reconstruction means size of the reconstruction region corresponding to the one of the reconstruction control modes.

3. The X-ray CT system according to claim 2, wherein
in the specified scan control mode, the transfer amount depends on one of a predetermined value, a heart rate and/or a respiratory rate, an ECG gated examination and/or a respiration gated examination, all phase imaging or partial phase imaging, and the size of the imaging region, or a combination of two or more thereof, while the scan control mode corresponds to the reconstruction control mode or is independent of the reconstruction control mode.

4. The X-ray CT system according to claim 2, wherein
the X-ray detecting means is configured to include X-ray detecting elements arranged in multiple rows in the longitudinal direction of the top board, and
the specified scan control mode refers to a relation table of the number of rows of the X-ray detecting elements used when the imaging regions are imaged and the transfer amount.

5. The X-ray CT system according to claim 3, wherein
the X-ray detecting means is configured to include X-ray detecting elements arranged in multiple rows in the longitudinal direction of the top board, and
the specified scan control mode refers to a relation table of the number of rows of the X-ray detecting elements used when the imaging regions are imaged and the transfer amount.

6. The X-ray CT system according to claim 2, wherein
the reconstruction means generates overlap regions with the adjacent pair of the imaging regions overlapping each other based on the projection data of the imaging regions, and
in the specified reconstruction control mode, the range of the overlap region depends on one of a predetermined value, a heart rate and/or a respiratory rate, an ECG gated examination and/or a respiration gated examination, all phase imaging or partial phase imaging, and the size of the imaging region, or a combination of two or more thereof, while the reconstruction control mode corresponds to the scan control mode or is independent of the scan control mode.

7. The X-ray CT system according to claim 2, wherein
the X-ray detecting means is configured to include X-ray detecting elements arranged in multiple rows in the longitudinal direction of the top board, and
the specified reconstruction control mode refers to a relation table of the number of rows of the X-ray detecting elements used when the imaging regions are imaged and the transfer amount.

8. The X-ray CT system according to claim 6, wherein
the X-ray detecting means is configured to include X-ray detecting elements arranged in multiple rows in the longitudinal direction of the top board, and
the specified reconstruction control mode refers to a relation table of the number of rows of the X-ray detecting elements used when the imaging regions are imaged and the transfer amount.

* * * * *